United States Patent
Eguchi

(10) Patent No.: US 9,661,728 B2
(45) Date of Patent: May 23, 2017

(54) RADIOGRAPHIC IMAGE PHOTOGRAPHING SYSTEM

(71) Applicant: Konica Minolta, Inc., Tokyo (JP)

(72) Inventor: Yoshihiko Eguchi, Tokorozawa (JP)

(73) Assignee: KONICA MINOLTA, INC., Tokyo (JP)

(*) Notice: Subject to any disclaimer, the term of this patent is extended or adjusted under 35 U.S.C. 154(b) by 407 days.

(21) Appl. No.: 13/892,776

(22) Filed: May 13, 2013

(65) Prior Publication Data

US 2013/0301802 A1 Nov. 14, 2013

(30) Foreign Application Priority Data

May 14, 2012 (JP) .................................. 2012-110490

(51) Int. Cl.
*A61B 6/00* (2006.01)
*H05G 1/08* (2006.01)

(52) U.S. Cl.
CPC ............. *H05G 1/08* (2013.01); *A61B 6/4283* (2013.01); *A61B 6/4494* (2013.01); *A61B 6/563* (2013.01)

(58) Field of Classification Search
CPC ..... A61B 6/4494; A61B 6/4405; A61B 6/563; A61B 6/565; H04L 67/125; G06F 19/32; G06F 19/321; H04W 84/12
See application file for complete search history.

(56) References Cited

U.S. PATENT DOCUMENTS

| 3,662,168 A | * | 5/1972 | Pelino ...................... B61K 9/06 104/307 |
| 2004/0088193 A1 | * | 5/2004 | Moriyama et al. ................ 705/3 |
| 2004/0193449 A1 | * | 9/2004 | Wildman et al. .................. 705/2 |
| 2005/0163285 A1 | * | 7/2005 | Kudo ...................... H01J 35/10 378/144 |

(Continued)

FOREIGN PATENT DOCUMENTS

| JP | 6-342099 A | 12/1994 |
| JP | 9-73144 A | 3/1997 |

(Continued)

OTHER PUBLICATIONS

Eguchi (WO2008/111355). Sep. 18, 2008.*

*Primary Examiner* — Dani Fox
(74) *Attorney, Agent, or Firm* — Cantor Colburn LLP

(57) ABSTRACT

The radiographic image photographing system includes an information acquisition member which acquires information on the radiographic image photographing device from an information presentation member of the radiographic image photographing device in a non-contact manner. When the information acquisition member makes the notification of the acquired information on the radiographic image photographing device, the management apparatus notifies the wireless communication member of the radiographic image photographing device of an identifier dedicated to an access point correlated with the information acquisition member. The wireless communication member of the radiographic image photographing device conducts wireless communication with the access point using a general-purpose identifier in a default state, and using the identifier dedicated to the access point after receiving the notification of the identifier dedicated to the access point from the management apparatus.

16 Claims, 10 Drawing Sheets

(56) References Cited

U.S. PATENT DOCUMENTS

| | | | |
|---|---|---|---|
| 2009/0196398 A1* | 8/2009 | Ohara | 378/98.5 |
| 2010/0148076 A1* | 6/2010 | Nishino et al. | 250/363.02 |
| 2010/0169423 A1* | 7/2010 | Eguchi | 709/204 |
| 2011/0069814 A1* | 3/2011 | Yonekawa | 378/62 |
| 2012/0045991 A1* | 2/2012 | Nonaka | 455/41.2 |
| 2012/0130902 A1* | 5/2012 | Dingler et al. | 705/71 |
| 2012/0206233 A1* | 8/2012 | Kamiya | A61B 6/4283 340/2.1 |
| 2012/0286167 A1* | 11/2012 | Eguchi | A61B 6/00 250/393 |
| 2013/0188629 A1* | 7/2013 | Lemaire et al. | 370/338 |

FOREIGN PATENT DOCUMENTS

| | | |
|---|---|---|
| JP | 2006-58124 A | 3/2006 |
| JP | 2012-11057 A | 1/2012 |

\* cited by examiner

FIG.6

| PHOTOGRAPHING ROOM Ra1 | INFORMATION ACQUISITION SECTION ID1 REPEATER ID1 |
|---|---|
| PHOTOGRAPHING ROOM Ra2 | INFORMATION ACQUISITION SECTION ID2 REPEATER ID2 |
| ⋮ | ⋮ |

FIG.7

| PHOTOGRAPHING ROOM Ra1 | INFORMATION ACQUISITION SECTION ID1 REPEATER ID1 | CASSETTE ID1 |
|---|---|---|
| PHOTOGRAPHING ROOM Ra2 | INFORMATION ACQUISITION SECTION ID2 REPEATER ID2 | |
| ⋮ | ⋮ | |

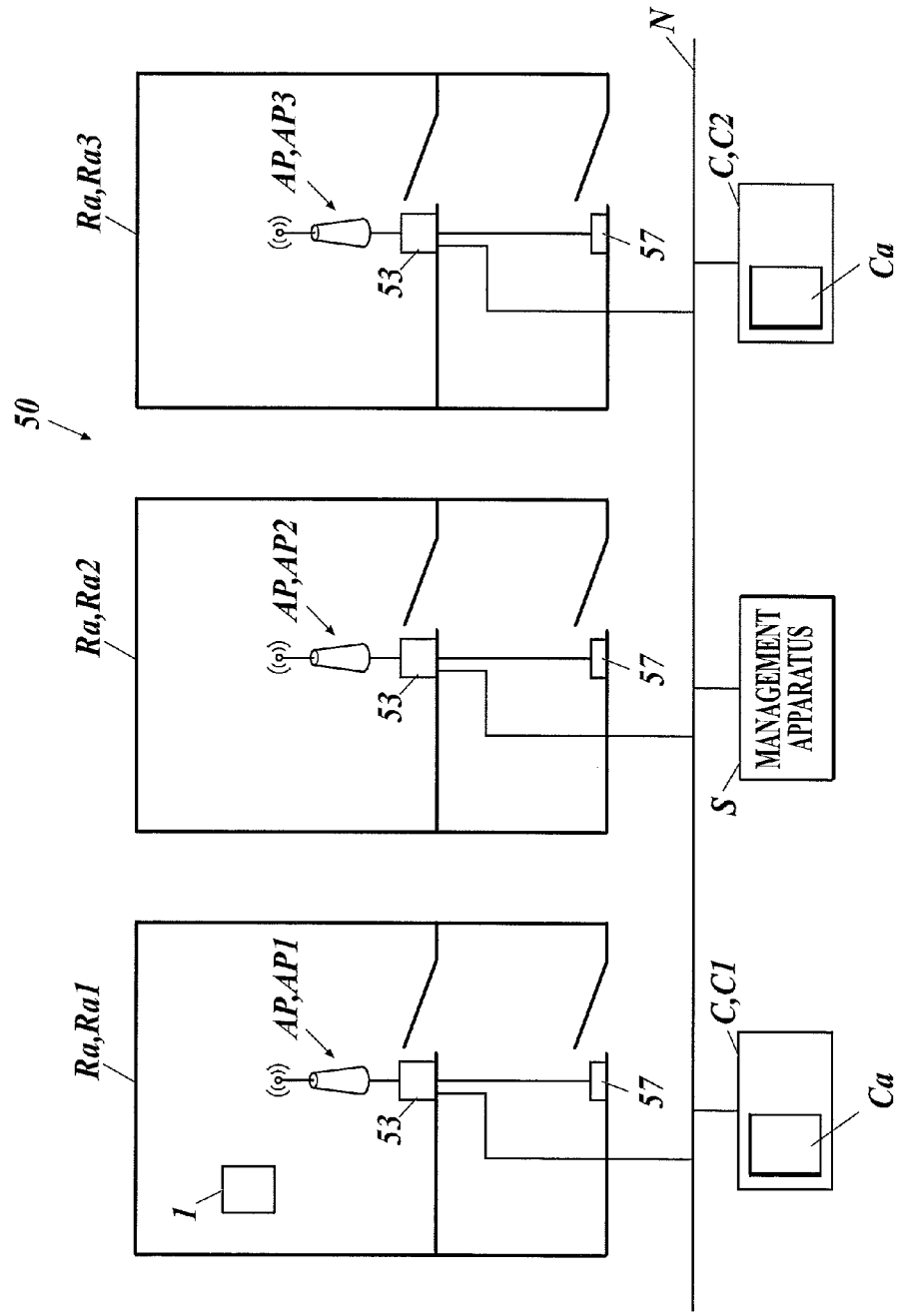

RADIOGRAPHIC IMAGE PHOTOGRAPHING SYSTEM

CROSS REFERENCE TO RELATED APPLICATIONS

The present invention claims priority under 35 U.S.C. §119 to Japanese Application No. 2012-110490 filed May 14, 2012, the entire content of which is incorporated herein by reference.

BACKGROUND

Field of the Invention

The present invention relates to a radiographic image photographing system, particularly to a radiographic image photographing system which uses a radiographic image photographing device.

Description of Related Art

There have been developed various radiographic image photographing devices such as a direct-type radiographic image photographing device which makes a detection element generate electrical charge corresponding to a dose of radiation such as an X-ray and converts the electrical charge to an electrical signal, and an indirect-type radiographic image photographing device which makes a scintillator or the like convert radiation into another electromagnetic wave such as visible light having a different wavelength, and then makes a photoelectric conversion element such as a photodiode generate the electrical charge corresponding to energy of the converted electromagnetic wave to convert the electrical charge to the electrical signal (or image data). In the present invention, the detection element in the direct-type radiographic image photographing device and the photoelectric conversion element in the indirect-type radiographic image photographing device are collectively referred to as a radiation detection element.

This type of radiographic image photographing device is well known as an FPD (Flat Panel Detector), and heretofore constituted as a so-called dedicated type (also referred to as a fixed-type or a stationary-type) integrally constituted with a support stage (for example, see Japanese Patent Application Laid-open No. 9-73144). Recently, a portable radiographic image photographing device whose casing houses the radiation detection element and the like so as to be carried by an operater is developed and put to practical use (for example, see Japanese Patent Application Laid-open No. 2006-058124 and Japanese Patent Application Laid-open No. 6-342099).

Such radiographic image photographing device includes a plurality of radiation detection elements which are usually arrayed in a two-dimensional (matrix) pattern on a sensor panel, and after being irradiated with the radiation through a subject to perform radiation image photographing, reads image data D from each of the radiation detection elements. The radiographic image photographing device is configured to perform radiation image photographing by exchanging data/signal between the radiographic image photographing device and an external device such as a console, for example by transmitting the read image data to the console.

Such transmission and reception of signal and the like between the radiographic image photographing device and the external device is performed by wireless LAN (Wireless Local Area Network, also referred to as a WLAN), for example. Sometimes a hospital facility has a plurality of photographing rooms, and access points are provided in the respective photographing rooms.

When the access points in the photographing rooms have the same identifier (for example, an SSID (Service Set Identifier) in the wireless LAN of IEEE 802.11), there is a possibility that wireless communication in a certain photographing room is received by an access point in another photographing room and a crossed line is generated. Therefore, in the case that the plurality of photographing rooms are provided, usually the identifiers at the access points in the photographing rooms differ from one another.

In the case that the radiographic image photographing device is the abovementioned portable type, since one radiographic image photographing device can be brought into any photographing rooms, it is necessary to perform processing to notify the radiographic image photographing device brought into a certain photographing room of the identifier of the access point in the photographing room.

Therefore, as disclosed in Japanese Patent Application Laid-open No. 2012-011057 for example, sometimes the radiographic image photographing device is configured to be inserted in a cradle placed in the photographing room in order to register existence of the radiographic image photographing device brought into the photographing room. It is possible to make the access point in the photographing room notified to the radiographic image photographing device inserted in the cradle.

However, there is a high possibility that an operator such as a radiology technician, who brings the radiographic image photographing device into the photographing room, forgets to insert the radiographic image photographing device in the cradle, and loads the radiographic image photographing device into a bucky device, for example. There is also a possibility that the operator feels troublesome for the necessity to insert the radiographic image photographing device brought into the photographing room in the cradle.

For the operator such as the radiology technician, the radiographic image photographing system including the radiographic image photographing device can be recognized as having good usability in the case that the radiographic image photographing device can automatically be registered and conduct wireless communication with the access point in the photographing room at a time point when the operator brings the radiographic image photographing device into the photographing room.

On the other hand, at the time point when the operator such as the radiology technician brings the radiographic image photographing device into the photographing room, the radiographic image photographing device does not learn the identifier of the access point in the photographing room. In this case, for example, it is necessary for the operator to input the identifier to the radiographic image photographing device. Therefore, the operator also feels troublesome.

As a result of investigation of a method for notifying the radiographic image photographing device of the identifier of the access point in the photographing room, the inventors have found a method for automatically, simply, and accurately notifying the radiographic image photographing device of the identifier of the access point in the photographing room.

SUMMARY

In view of the foregoing, an object of the present invention is to provide a radiographic image photographing system which can automatically, simply, and accurately notify the radiographic image photographing device of the identifier of the access point.

To solve the above-described problem, according to an aspect of a preferred embodiment of the present invention, there is provided a radiographic image photographing system including:

a portable radiographic image photographing device which includes: a plurality of radiation detection elements arrayed in a two-dimensional pattern; a wireless communication member to conduct wireless communication; and an information presentation member to present information on the radiographic image photographing device;

a console which is communicable with the radiographic image photographing device;

an access point which relays wireless communication conducted between the wireless communication member in the radiographic image photographing device and the console;

an information acquisition member which acquires the information on the radiographic image photographing device from the information presentation member in the radiographic image photographing device in a non-contact manner; and a management apparatus to which at least the access point and the information acquisition member are connected, wherein the management apparatus notifies the wireless communication member in the radiographic image photographing device of an identifier dedicated to the access point correlated with the information acquisition member when the information acquisition member notifies the management apparatus of the information on the radiographic image photographing device, which information is acquired from the information presentation member in the radiographic image photographing device, the wireless communication member in the radiographic image photographing device includes a general-purpose identifier which is communicable with any of the access point, the wireless communication member in a default state conducts communication with the access point using the general-purpose identifier, and the wireless communication member conducts communication with the access point using the identifier dedicated to the access point after the management apparatus notifies the wireless communication member in the radiographic image photographing device of the identifier dedicated to the access point.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 6 is a view illustrating an example of a table in which the photographing room is correlated with an information acquisition member ID and a repeater ID;

FIG. 7 is a view illustrating a state in which a cassette ID is correlated with a photographing room Ra1;

FIG. 9 is a view illustrating a configuration example of the radiographic image photographing system in which the console is connected to a plurality of photographing rooms through a network;

DETAILED DESCRIPTION OF THE PREFERRED EMBODIMENT

A radiographic image photographing system according to an embodiment of the present invention will be described with reference to the drawings.

Hereinafter, a so-called indirect-type radiographic image photographing device, which includes a scintillator or the like to convert emitted radiation into an electromagnetic wave such as a visible light having a different wavelength to obtain an electrical signal, will be described as a radiographic image photographing device of the present invention. However, the present invention can also be applied to a so-called direct-type radiographic image photographing device which directly detects radiation by the radiation detection element without using the scintillator or the like.

[Configuration of Radiographic Image Photographing System]

Figure 1:
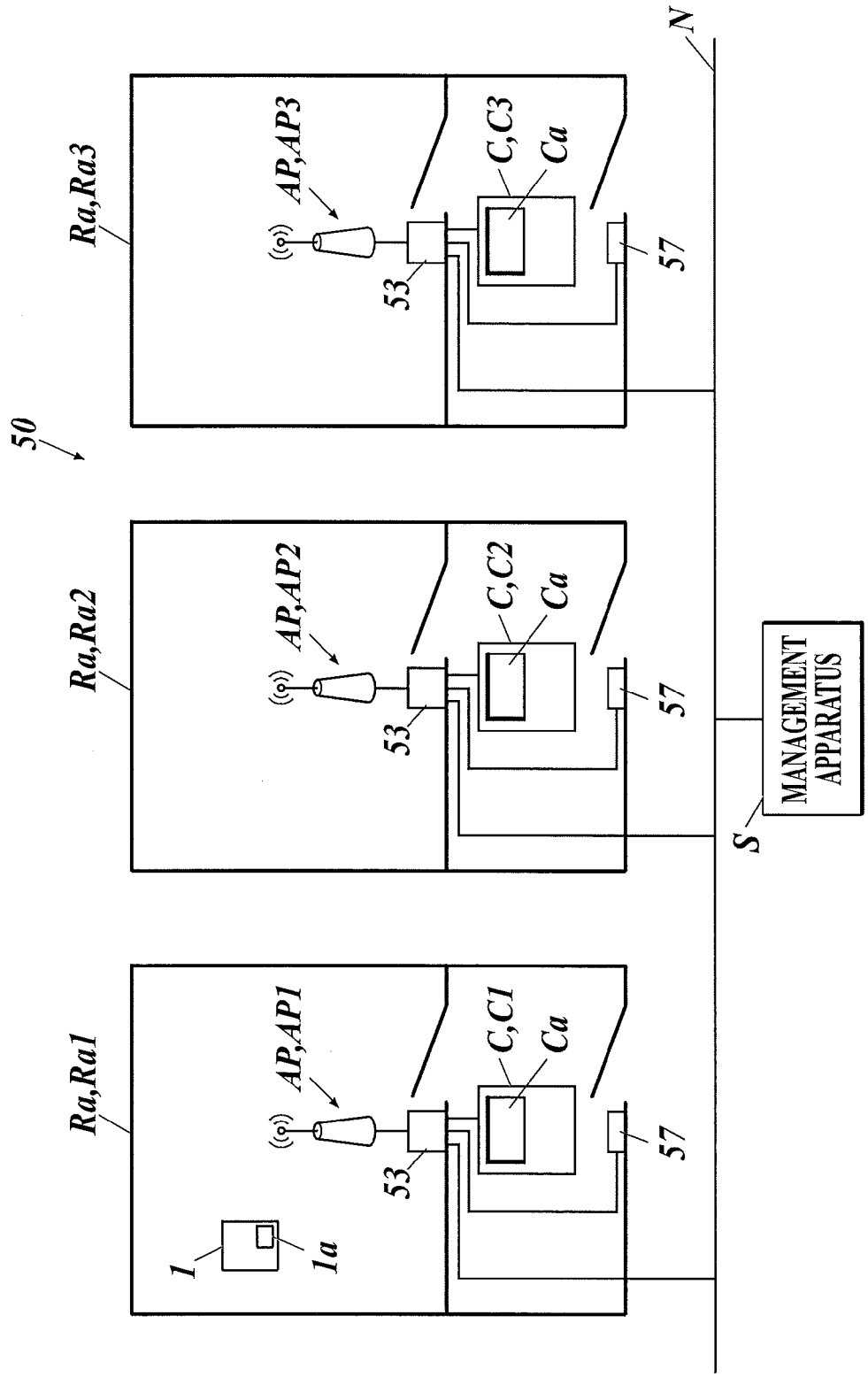
FIG. 1 is a diagram illustrating a configuration example of a radiographic image photographing system according to an embodiment.

A configuration of a radiographic image photographing system 50 according to the embodiment will be firstly described. As illustrated in FIG. 1, the embodiment shows the case where the radiographic image photographing system 50 includes a plurality of photographing rooms Ra1, Ra2, . . . , and a console C is provided in each of the photographing rooms Ra1, Ra2, . . . .

Incidentally, a radiographic image photographing system of another embodiment will be described later. In the embodiment, the console C functions as an image processing device which generates a radiation image based on image data D and the like transmitted from a radiographic image photographing device 1. Alternatively, the image processing device may be configured to be separated from the console.

In the embodiment, as illustrated in FIG. 1, the radiographic image photographing system 50 includes a plurality of photographing rooms Ra, and an access point AP and the console C are provided in each of the photographing rooms Ra. The access point AP and the console C are connected to a network N through a repeater 53 provided in each of the photographing rooms Ra, and a management apparatus S is connected to the network N.

Although not illustrated, necessary instruments and facilities, such as an HIS (Hospital Information System), an RIS (Radiology Information System), another computer, and such an external instrument as an imager which records the radiation image in an image recording medium such as a film and outputs the radiation image, are connected to the network N.

[Configuration of Radiographic Image Photographing Device]

Figure 2:
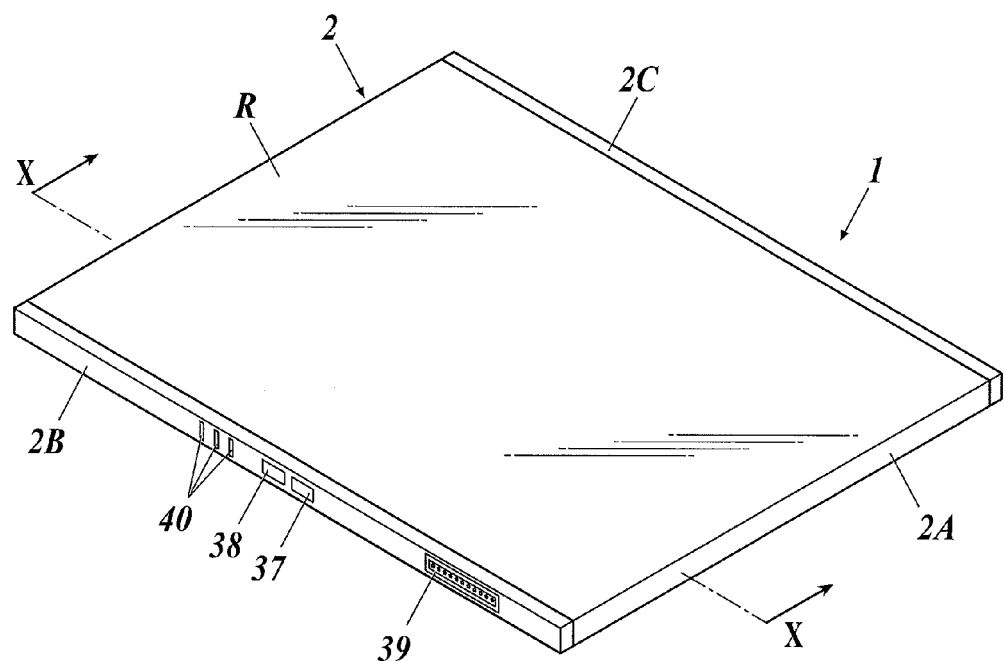
FIG. 2 is a perspective view illustrating an appearance of the radiographic image photographing device of the embodiment.

Next, a configuration of the radiographic image photographing device 1 will be described before the configuration of the photographing room Ra is described. FIG. 2 is a perspective view illustrating an appearance of the radiographic image photographing device, and FIG. 3 is a sectional view of the radiographic image photographing device.

As illustrated in FIG. 2, the radiographic image photographing device 1 is a portable type in which a sensor panel SP including a scintillator 3 and a board 4 is accommodated in a casing 2 including a radiation incident surface R which is on a side irradiated with the radiation. Although not illustrated in FIG. 2, an antenna device 41 (see FIG. 4) is provided in the casing 2 of the radiographic image photographing device 1 in order to conduct wireless communication with an external device such as the console C and the management apparatus S through the access point AP to be described later.

In FIG. 2, the reference sign 37 designates a power switch, the reference sign 38 designates a selector switch, and the reference sign 40 designates an indicator which is composed of an LED or the like to display a battery state or an operating state of the radiographic image photographing device 1.

Figure 3:
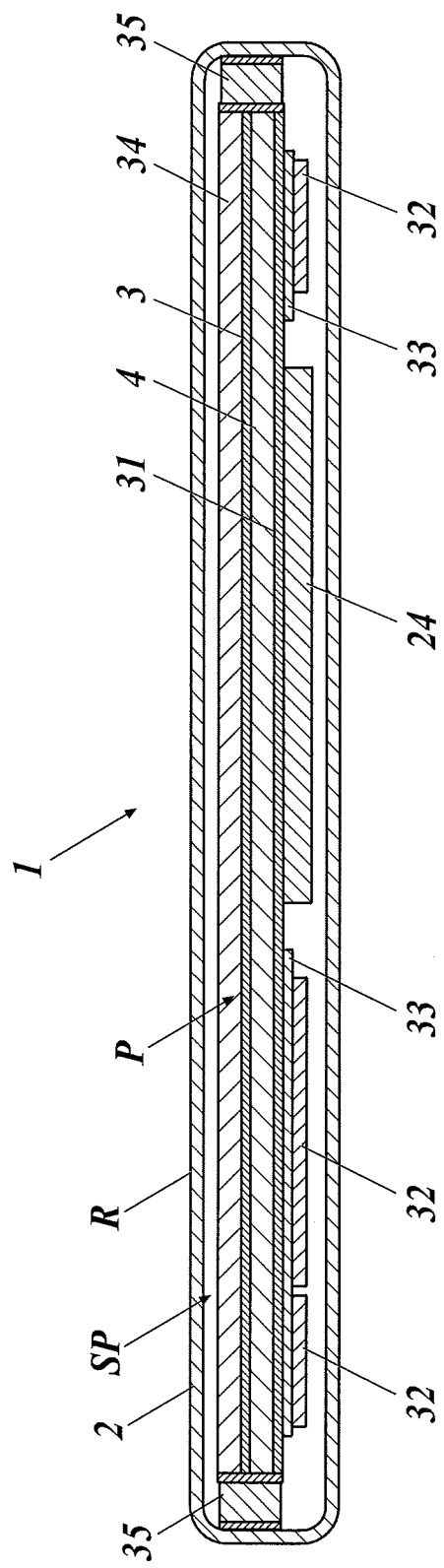
FIG. 3 is a sectional view of the radiographic image photographing device of the embodiment.

As illustrated in FIG. 3, a base 31 is disposed in the casing 2, and the board 4 is provided on the side (hereinafter simply referred to as an upper side) of the base 31, which side is near the radiation incident surface R, with a lead thin plate (not illustrated) interposed therebetween. The scintillator 3 put on a scintillator board 34 is disposed on the side (upper side) of the board 4, which side is near the radiation incident surface R, so that the scintillator 3 is opposite to the board 4.

On a lower side of the base 31, a PCB board 33 on which an electronic component 32 and the like are disposed and a battery 24 are attached. Thus, the sensor panel SP is composed of the base 31, the board 4, and the like. In the embodiment, buffer materials 35 are provided between the sensor panel SP and both sides of the casing 2.

Figure 4:
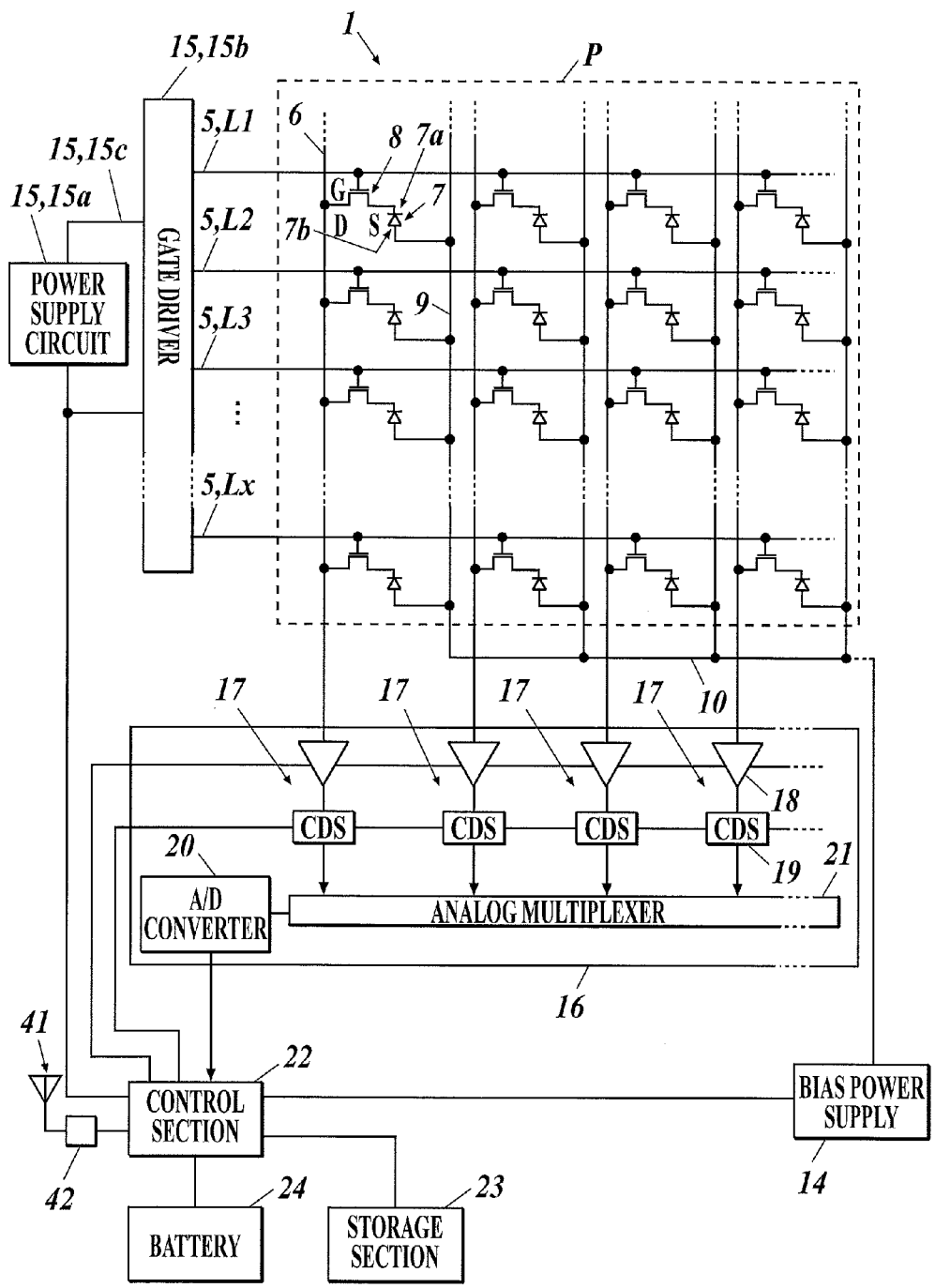
FIG. 4 is a block diagram illustrating an equivalent circuit of the radiographic image photographing device of the embodiment.

A circuit configuration of the radiographic image photographing device 1 will be described below. FIG. 4 is a block diagram illustrating an equivalent circuit of the radiographic image photographing device.

A plurality of scanning lines 5 and a plurality of signal lines 6 are disposed so as to intersect one another on an upper side (or a side opposite to the scintillator 3) of the board 4 of the radiographic image photographing device 1. A radiation detection element 7 is provided in each small area partitioned by the scanning lines 5 and the signal lines 6.

In the radiographic image photographing device 1, a plurality of radiation detection elements 7 are arrayed in a two-dimensional (matrix) pattern, and the whole area where the radiation detection elements 7 are provided, namely, the area indicated by an alternate long and short dash line in FIG. 4 constitutes a detection section P. In the embodiment, a photodiode is used as the radiation detection element 7. Alternatively, for example, other radiation detection elements such as a phototransistor may be used.

A source electrode 8s (see "S" in FIG. 4) of a TFT 8 which is a switch element is connected to a first electrode 7a of each radiation detection element 7. A drain electrode 8d and a gate electrode 8g (see "D" and "G" in FIG. 4) of the TFT 8 are connected to the signal line 6 and the scanning line 5, respectively.

In the embodiment, as illustrated in FIG. 4, bias lines 9 are provided for respective columns of radiation detection elements 7, and each bias line 9 is connected to second electrodes 7b of the radiation detection elements 7. The bias lines 9 are connected to a wire connection 10 in a position outside the detection section P of the board 4. The wire connection 10 is connected to a bias power supply 14, and a reverse bias voltage is applied to each of the second electrodes 7b of radiation detection elements 7 from the bias power supply 14 through the wire connection 10 and the bias line 9.

Meanwhile, the scanning lines 5 are connected to a gate driver 15b of a scanning drive member 15. In the scanning drive member 15, an on-voltage and an off-voltage are supplied to the gate driver 15b from a power supply circuit 15a through a wiring 15c. The gate driver 15b switches a voltage applied to each of lines L1 to Lx of the scanning lines 5 between the on-voltage and the off-voltage, thereby controlling an on/off operation of each TFT 8.

Each of signal lines 6 is connected to each of readout circuits 17 incorporated in a readout IC 16 through each input/output terminal. In the embodiment, each of the readout circuits 17 mainly includes an amplifier circuit 18 and a correlated double sampling circuit 19. An analog multiplexer 21 and an A/D converter 20 are provided in the readout IC 16. In FIG. 4, the correlated double sampling circuit 19 is abbreviated to a CDS.

In the embodiment, in readout processing of reading image data D from each of the radiation detection elements 7 after photographing of the radiation image, electrical charge generated and accumulated in the radiation detection elements 7 flow out from each of the radiation detection elements 7 to the signal line 6 through the TFT 8, which has been put into an on-state by applying the on-voltage from the gate driver 15b through the scanning line 5.

From output of the amplifier circuit 18, a voltage value is output according to an amount of electrical charge flowing in through the signal line 6. The correlated double sampling circuit 19 outputs an increase of the output value from the amplifier circuit 18 before and after the electrical charge flows in from each of the radiation detection elements 7 toward a downstream direction as the analog image data D.

The output pieces of image data D are sequentially transmitted to the A/D converter 20 through the analog multiplexer 21, and the A/D converter 20 sequentially converts the analog image data D into the digital image data D, and outputs the digital image data D to a storage member 23 to store the digital image data D in the storage member 23. Thus, the readout processing of reading the image data D is performed.

A control member 22 includes a CPU (Central Processing Unit), ROM (Read Only Memory), RAM (Random Access Memory), a computer in which an input/output interface is connected to a bus, and an FPGA (Field Programmable Gate Array), which are not illustrated. The control member 22 may be composed of a dedicated control circuit.

The control member 22 controls an operation of each functional member/section of the radiographic image photographing device 1, to control the scanning drive member 15 or the readout circuit 17 to perform the readout processing of reading the image data D, for example. As illustrated in FIG. 4, the storage member 23 including an SRAM (Static RAM) and an SDRAM (Synchronous DRAM) is connected to the control member 22.

To the control member 22, a battery 24 which supplies a power necessary for the functional members/sections, such as the scanning drive member 15, the readout circuit 17, the storage member 23, and the bias power supply 14, is connected.

To the control member 22, also a wireless communication section 42 as a wireless communication member including the antenna device 41 is connected, and the wireless communication section 42 conducts wireless communication of signals and the like with the external device through the antenna device 41. In the embodiment, for example, the wireless communication section 42 conducts wireless communication with the external device by wireless LAN pursuant to IEEE 802.11.

A function unique to the wireless communication section 42 of the radiographic image photographing device 1 in the radiographic image photographing system 50 of the embodiment is described in detail later.

[Configuration of Photographing Room]

Figure 5:
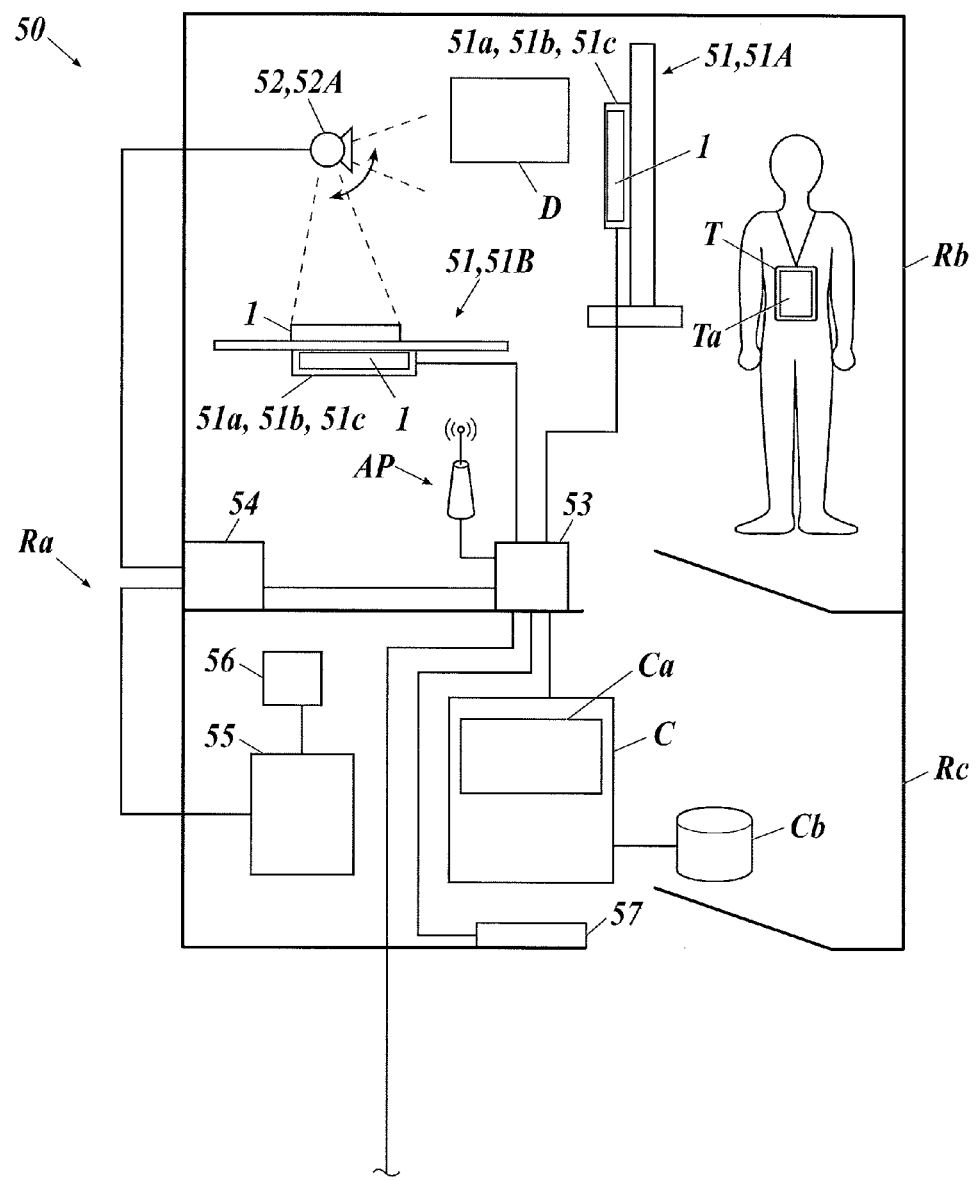
FIG. 5 is a view illustrating a configuration of each photographing room.

A structure in the photographing room Ra will be described below. The photographing room Ra is a room in which a region of a patient body to be photographed, namely, a photographing region of a subject is irradiated with the radiation to perform the radiation image photographing. FIG. 5 is a view illustrating a configuration of each photographing room. Incidentally, the display member D and the mobile terminal T including the display screen Ta are optional members in the configuration of the embodiment, and they will be described later.

A bucky device (also referred to as a bucky photographing stage) 51 is placed in a so-called photographing room Rb of the photographing room Ra, and the bucky device 51 can be used while the radiographic image photographing device 1 is loaded into a cassette retention section (also referred to as a cassette holder) 51a of the bucky device 51. FIG. 5 illustrates the case that a bucky device 51A for photographing an upright position and a bucky device 51B for photographing a supine position are placed as the bucky device 51. Alternatively, for example, only one of the bucky devices 51A and 51B may be provided.

As illustrated in FIG. 5, at least one radiation source 52 is provided in the photographing room Rb in order to irradiate the radiographic image photographing device 1 loaded into the bucky device 51 with the radiation through the subject. In the embodiment, both the bucky device 51A for photographing the upright position and the bucky device 51B for photographing the supine position can be irradiated with the radiation by moving the radiation source 52 or changing an irradiation direction of the radiation.

A repeater (also referred to as a base station) 53 is provided in the photographing room Rb in order to relay communication between each device in the photographing room Rb and each device outside the photographing room Rb. The access point AP is provided in the repeater 53 such that the radiographic image photographing device 1 can conduct wireless communication.

The repeater 53 is connected to a radiation generating device 54, the console C and so on, and also connected to the management apparatus S through the network N as illustrated in FIG. 1. A converter (not illustrated) is incorporated in the repeater 53. The converter converts the signal for LAN communication, such as Ethernet (registered trademark), which is transmitted to the radiation generating device 54 from the radiographic image photographing device 1 or the console C, into the signal for the radiation generating device 54, and the converter also performs reverse conversion.

In the embodiment, when the radiographic image photographing device 1 transmits the data and the signal to the console C or the management apparatus S, the repeater 53 transmits the data while identification information (hereinafter referred to as a repeater ID) on the repeater 53 is attached to the data.

In the embodiment, an operator station 55 of the radiation generating device 54 is provided in a front room (also referred to as an operator room) Rc of the photographing room Ra, and an exposure switch 56 is provided in the operator station 55 in order that the operator such as the radiology technician operates to issue an instruction to the radiation generating device 54 to start the irradiation. In the radiation generating device 54, the radiation source 52 emits the radiation when the operator operates the exposure switch 56. The radiation generating device 54 performs various kinds of control, such as adjustment of the radiation source 52, such that the proper dose of the radiation is obtained.

Moreover, the console C is provided in the front room Rc as illustrated in FIG. 5 in the embodiment. The console C includes a CPU (Central Processing Unit), ROM (Read Only Memory), RAM (Random Access Memory), and a computer in which an input/output interface is connected to a bus, which are not illustrated. The console C may be configured to be provided in another appropriate position, for example outside the photographing room Rb or the front room Rc, or in another room.

The console C is provided with a display section Ca including a CRT (Cathode Ray Tube) or an LCD (Liquid Crystal Display). A storage member Cb including an HDD (Hard Disk Drive) is connected to or incorporated in the console C.

As illustrated in FIG. 5, the radiographic image photographing device 1 can be inserted between a body of a patient (not illustrated) lying on the bucky device 51B for photographing the supine position in the photographing room Rb, and the bucky device 51B, or the radiographic image photographing device 1 can be placed onto the body of the patient on the bucky device 51B for photographing the supine position. In such cases, both the radiation source 52 installed in the photographing room Rb and a portable radiation source (not illustrated) can be used.

In the embodiment, the console C controls an activation state of the radiographic image photographing device 1, by transmitting a signal to the radiographic image photographing device 1 to wake it up or bring it to a sleep state, for example. The console C also controls the radiation generating device 54 by issuing an instruction to the radiation generating device 54 to supply a tube voltage or the like to the radiation source 52.

When the image data D is transmitted to the console C from the radiographic image photographing device 1, the console C displays a preview image on the display section Ca based on the image data D, or the console C more strictly performs image processing to the image data D to generate the radiation image.

Meanwhile, as shown in FIG. 1, a so-called RFID (Radio Frequency Identification) tag is incorporated inside the radiographic image photographing device 1 as an information presentation member 1a which informs information such as own identification information (hereinafter referred to as a cassette ID), namely information of the radiographic image photographing device 1, in the embodiment.

Near an entrance of the photographing room Rb and/or the front room Rc, a tag reader 57 is provided as the information acquisition member. The tag reader 57 acquires the information on the radiographic image photographing device 1 from the RFID tag as the information presentation member 1a of the radiographic image photographing device 1 in a non-contact manner. When the radiographic image photographing device 1 is brought into the photographing room Ra, the tag reader 57 decodes the information on the radiographic image photographing device 1 including the cassette ID from an electromagnetic field or a radio wave, which is emitted from the RFID tag of the radiographic image photographing device 1, thereby acquiring the information on the radiographic image photographing device 1 from the RFID tag of the radiographic image photographing device 1 without physically contacting the RFID tag.

In the embodiment, the tag reader 57 as the information acquisition member attaches own identification information (hereinafter referred to as an information acquisition member ID) to the decoded information on the radiographic image photographing device 1, and notifies the management apparatus S (see FIG. 1) of the information on the radiographic image photographing device 1 through the repeater 53.

Other embodiments of the information presentation member 1a of the radiographic image photographing device 1 and the information acquisition member which acquires the information on the radiographic image photographing device 1 in the non-contact manner are described later.

[Management Apparatus]

Next, the management apparatus S will be described. In the embodiment, the management apparatus S is constructed by a server computer or the like. As illustrated in FIG. 1, the management apparatus S is connected to the access point AP in each of the photographing rooms Ra, the information acquisition member (or the tag reader 57 in the embodiment), the console C and so on, through the network N and the repeater 53 in each of the photographing rooms Ra.

Although not illustrated in FIG. 1, a storage member composed of the HDD or the like is connected to or incorporated in the management apparatus S. The processing in the management apparatus S will be described in description of the radiographic image photographing system 50 of the embodiment.

[Radiographic Image Photographing System]

Next, the configuration of the radiographic image photographing system 50 in the embodiment will be described, which configuration is for solving the abovementioned problem, namely for automatically, simply, and accurately inform the identifier of the access point AP (see FIG. 1 or 5) of the photographing room Ra to the radiographic image photographing device 1 without the operation of the operator such as the radiology technician for inputting the identifier in the radiographic image photographing device 1.

Also a function of the radiographic image photographing system 50 in the embodiment will be described together with the configuration. In the embodiment, the wireless LAN of IEEE 802.11 is used as the wireless communication system, and hereinafter the identifier of the access point AP is described as the SSID. In the case that another system of wireless communication is used, the identifier suitable to the wireless communication system is used as the identifier of the access point SP.

In the embodiment, a different SSID is assigned to the access point AP in each of the photographing rooms Ra. Hereinafter, the SSID in each access point AP is referred to as an SSID 1.

At the access point AP in the photographing room Ra, the wireless communication can also be conducted using a general-purpose SSID as a general-purpose identifier which enables communication with any (of) access point(s) AP. Hereinafter, the general-purpose SSID is referred to as an SSID 2. The wireless communication section 42 (see FIG. 4) of the radiographic image photographing device 1 has the SSID 2 as the general-purpose identifier, and the wireless communication section 42 in a default state conducts communication with the access point AP using the SSID 2.

The case that the operator such as the radiology technician brings the radiographic image photographing device 1 into the photographing room Ra (for example, a photographing room Ra1) will specifically be described below.

In the management apparatus S of the embodiment, the identification information on the tag reader 57 as the information acquisition member provided in each of the photographing rooms Ra, namely, the information acquisition member ID, and/or the identification information on the repeater 53 provided in each of the photographing rooms Ra, namely, the repeater ID, are previously correlated with the photographing room Ra, and they are stored in the storage member, for example, in a form of a table as shown in FIG. 6.

When the radiographic image photographing device 1 is brought into the photographing room Ra (for example, the photographing room Ra1), the tag reader 57 as the information acquisition member in the photographing room Ra1 acquires the information on the radiographic image photographing device 1 such as the cassette ID from the RFID tag as the information presentation member 1a of the radiographic image photographing device 1, as described above. The tag reader 57 makes notification to the management apparatus S while the information acquisition member ID as the own identification information is attached to the acquired information on the radiographic image photographing device 1.

When the tag reader 57 makes a notification of the information on the radiographic image photographing device 1, to which the information acquisition member ID is attached, the management apparatus S identifies the photographing room Ra (in this case, the photographing room Ra1) correlated with the information acquisition member ID and/or repeater ID, based on the information acquisition member ID attached to the cassette ID, and/or the repeater ID as the identification information on the repeater 53 which relays the information acquisition member ID, in the photographing room Ra1.

As illustrated in FIG. 7, the management apparatus S correlates the notified cassette ID with the identified photographing room Ra1. Thus, in the embodiment, the management apparatus S performs management by recognizing which of the photographing rooms Ra the radiographic image photographing device 1 exists in (in this case, the radiographic image photographing device 1 exists in the photographing room Ra1), based on the information acquisition member ID attached to the cassette ID, and/or the repeater ID as the identification information on the repeater 53 which relays the information acquisition member ID.

FIG. 7 illustrates the case that the radiographic image photographing device 1 is brought into the photographing room Ra1 while the radiographic image photographing device 1 is not brought into other photographing rooms Ra2, . . . .

As can be seen from FIGS. 6 and 7, both the information acquisition member ID and the repeater ID are not necessarily correlated with the photographing room Ra unlike the embodiment. When at least one of the pieces of identification information (that is, the information acquisition member ID or the repeater ID) is correlated with the photographing room Ra, which of the photographing rooms Ra the radiographic image photographing device 1 exists in can be recognized to perform the management.

Meanwhile, when the tag reader 57 as the information acquisition member makes the notification of the information on the radiographic image photographing device 1, the management apparatus S conducts wireless communication with the wireless communication section 42 (see FIG. 4) of the radiographic image photographing device 1 through the access point AP1 of the identified photographing room Ra1 using the SSID 2 as the general-purpose identifier. The management apparatus S notifies the wireless communication section 42 of the access point AP1 correlated with the tag reader 57, namely, the SSID 1 as the identifier dedicated to the access point AP1 provided in the photographing room Ra1.

After receiving the notification of the SSID 1 as the identifier dedicated to the access point AP1 from the management apparatus S, the wireless communication section 42 of the radiographic image photographing device 1 switches the state in which wireless communication is conducted with the access point AP1 using the SSID 2 as the general-purpose identifier to the state in which wireless communication is conducted with the access point AP1 using the SSID 1 dedicated to the access point AP1.

Thus, in the embodiment, the wireless communication section 42 of the radiographic image photographing device 1 conducts wireless communication with the access point AP1 using the general-purpose SSID 2 until the wireless communication section 42 receives the notification of the SSID 1 as the identifier dedicated to the access point AP1 from the management apparatus S. Therefore, the wireless communication section 42 can conduct wireless communication with any one of the access points AP2, . . . in the photographing rooms Ra2, . . . .

Therefore, even when the radiographic image photographing device 1 exists in any of the photographing rooms Ra, the management apparatus S can accurately conduct wireless communication with the radiographic image photographing device 1 using the general-purpose SSID 2.

In the embodiment, the wireless communication section 42 of the radiographic image photographing device 1 conducts wireless communication with the access point AP1 using the SSID 1 dedicated to the access point AP1 after the wireless communication section 42 receives the notification of the SSID 1 as the identifier dedicated to the access point AP1 from the management apparatus S.

According to this configuration, the crossed line caused by receiving the wireless communication at the access point AP in another photographing room Ra is not generated, and the radiographic image photographing device 1 existing in certain photographing room Ra can accurately conduct wireless communication through the access point AP provided in the certain photographing room Ra.

Unlike the case mentioned in abovementioned Japanese Patent Application Laid-open No. 2012-011057, when the operator such as the radiology technician brings the radiographic image photographing device 1 into the photographing room Ra, without setting the SSID 1 dedicated to the access point AP in the photographing room Ra by inserting the radiographic image photographing device 1 into the cradle provided in the photographing room Ra or inputting the SSID 1 by the operator, the SSID is automatically set in the radiographic image photographing device 1 in a non-contact manner through the above procedure.

In the radiographic image photographing system 50 of the embodiment, the radiographic image photographing device 1 can automatically and simply be notified in the non-contact manner of the SSID 1 as the identifier dedicated to the access point AP in the photographing room Ra, and the SSID 1 can accurately be set. Therefore, it becomes unnecessary for the operator such as the radiology technician to insert the radiographic image photographing device 1 into the cradle or to input the SSID 1 by himself, and the radiographic image photographing system 50 can achieve great usability for the operator.

Meanwhile, the management apparatus S of the embodiment informs, to the wireless communication section 42 of the radiographic image photographing device 1, both the SSID 1 dedicated to the access point AP1 in the photographing room Ra1 and the necessary information such as the information (for example, an IP address (Internet Protocol address) on the network) on the network setting of the console C1 (see FIG. 1) in the photographing room Ra1.

When receiving the notification of the information on the network setting of the console C1 from the management apparatus S, the wireless communication section 42 of the radiographic image photographing device 1 notifies the console C1 of the own information on the network setting, namely, the necessary information such as the own cassette ID and IP address through the access point AP1 using the SSID 1.

Thus, in the embodiment, the radiographic image photographing device 1 and console C1 in the photographing room Ra1 are linked to each other through the access point AP1. Incidentally, instead of notifying the console C1 of the IP address by the radiographic image photographing device 1 itself, the management apparatus S may notify the console C1 in the photographing room Ra1 of the necessary information such as the IP address of the wireless communication section 42 of the radiographic image photographing device 1 brought into the photographing room Ra1.

According to the above configuration, the wireless communication section 42 of the radiographic image photographing device 1 brought into the photographing room Ra1 and the console C1 of the photographing room Ra1 can directly conduct wireless communication with each other using the SSID 1 dedicated to the access point AP1 in the photographing room Ra1, and the data/signal can directly and accurately be exchanged between the radiographic image photographing device 1 and the console C1 without generating the crossed line with the access points AP in other photographing rooms Ra.

In the embodiment, after the wireless communication between the radiographic image photographing device 1 and the console C1 is established using the SSID 1, whether or not the wireless communication is conducted between radiographic image photographing device 1 and the console C using the SSID 1 is periodically (for example, every 10 seconds) checked.

While the wireless communication is confirmed (that is, while the wireless communication is periodically conducted between the radiographic image photographing device 1 and the console C1 using the SSID 1), the management apparatus S maintains the correlation of the radiographic image photographing device 1 with the photographing room Ra1.

At a time point when the wireless communication cannot be confirmed, the management apparatus S terminates the correlation of the radiographic image photographing device 1 with the photographing room Ra1. This is because the radiographic image photographing device 1 can be determined to be brought out from the photographing room Ra1, or the SSID 1 can be determined to be switched to the general-purpose SSID 2 when the operator such as the radiology technician brings out the radiographic image photographing device 1 from the photographing room Ra1, for example.

Meanwhile, the wireless communication section 42 of the radiographic image photographing device 1 of the embodiment determines, when the operator such as the radiology technician switches the SSID 1 to the general-purpose SSID 2, or when the wireless communication with the access point AP1 cannot be periodically confirmed, that the wireless communication cannot be conducted using the SSID 1, and the wireless communication section 42 returns the identifier for the wireless communication to the general-purpose SSID 2 in the default state.

Then, when the radiographic image photographing device 1 is brought into the photographing room Ra2 (see FIG. 1) for example, the processing is performed in the same procedure. The radiographic image photographing device 1 is correlated with the photographing room Ra2 in the management apparatus S, and at the same time, the SSID 1 dedicated to the access point AP2 in the photographing room Ra2 is informed to the wireless communication section 42 of the radiographic image photographing device 1 and the SSID 1 is set.

In the case that the radiographic image photographing system 50 includes a plurality of the radiographic image photographing devices 1, the management apparatus S is configured to perform the same processing to each of the radiographic image photographing devices 1, notifies the wireless communication section 42 of each radiographic image photographing device 1 of the SSID 1 dedicated to the access point AP in the photographing room Ra in which the radiographic image photographing device 1 exists, and correlates each radiographic image photographing device 1 with one of the photographing rooms Ra shown in FIG. 7.

As described above, according to the radiographic image photographing system 50 of the embodiment, since the wireless communication section 42 of the radiographic image photographing device 1 in the default state conducts wireless communication with the access point AP1 using the general-purpose SSID 2, the wireless communication section 42 can conduct wireless communication with any of access points AP in the photographing rooms Ra. Therefore, even when the radiographic image photographing device 1 exists in any of photographing rooms Ra, the management apparatus S can accurately conduct wireless communication with the radiographic image photographing device 1 using the general-purpose SSID 2, and the management apparatus S can inform the SSID 1 dedicated to the access point AP in the photographing room Ra in which the radiographic image photographing device 1 exists to the wireless communication section 42 of the radiographic image photographing device 1.

Moreover, the wireless communication section 42 of the radiographic image photographing device 1 of the embodiment conducts wireless communication with the access point AP1 using the SSID 1 dedicated to the access point AP1 after receiving the notification of the SSID 1 as the identifier dedicated to the access point AP1 from the management apparatus S. For this reason, the crossed line caused by the reception of the wireless communication at the access point AP in another photographing room Ra is not generated, and the radiographic image photographing device 1 existing in the photographing room Ra can accurately conduct wireless communication through only the access point AP provided in the photographing room Ra.

Furthermore, the SSID 1 dedicated to the access point AP in the photographing room Ra is automatically set to the radiographic image photographing device 1 in the non-contact manner through the above procedure when the radiographic image photographing device 1 is brought into the photographing room Ra, without the setting of the SSID 1 in the radiographic image photographing device 1 by the operator such as the radiology technician, concretely without inserting the radiographic image photographing device 1 in the cradle provided in the photographing room Ra or inputting the SSID 1, for example.

Thus, according to the radiographic image photographing system 50 of the embodiment, the radiographic image photographing device 1 can automatically and simply be notified in the non-contact manner of the SSID 1 as the identifier dedicated to the access point AP in the photographing room Ra, and the SSID 1 can accurately be set to the wireless communication section 42 of the radiographic image photographing device 1. Therefore, it becomes unnecessary for the operator to insert the radiographic image photographing device 1 in the cradle or to input the SSID 1 by himself, and the radiographic image photographing system 50 can achieve great usability.

Figure 8:
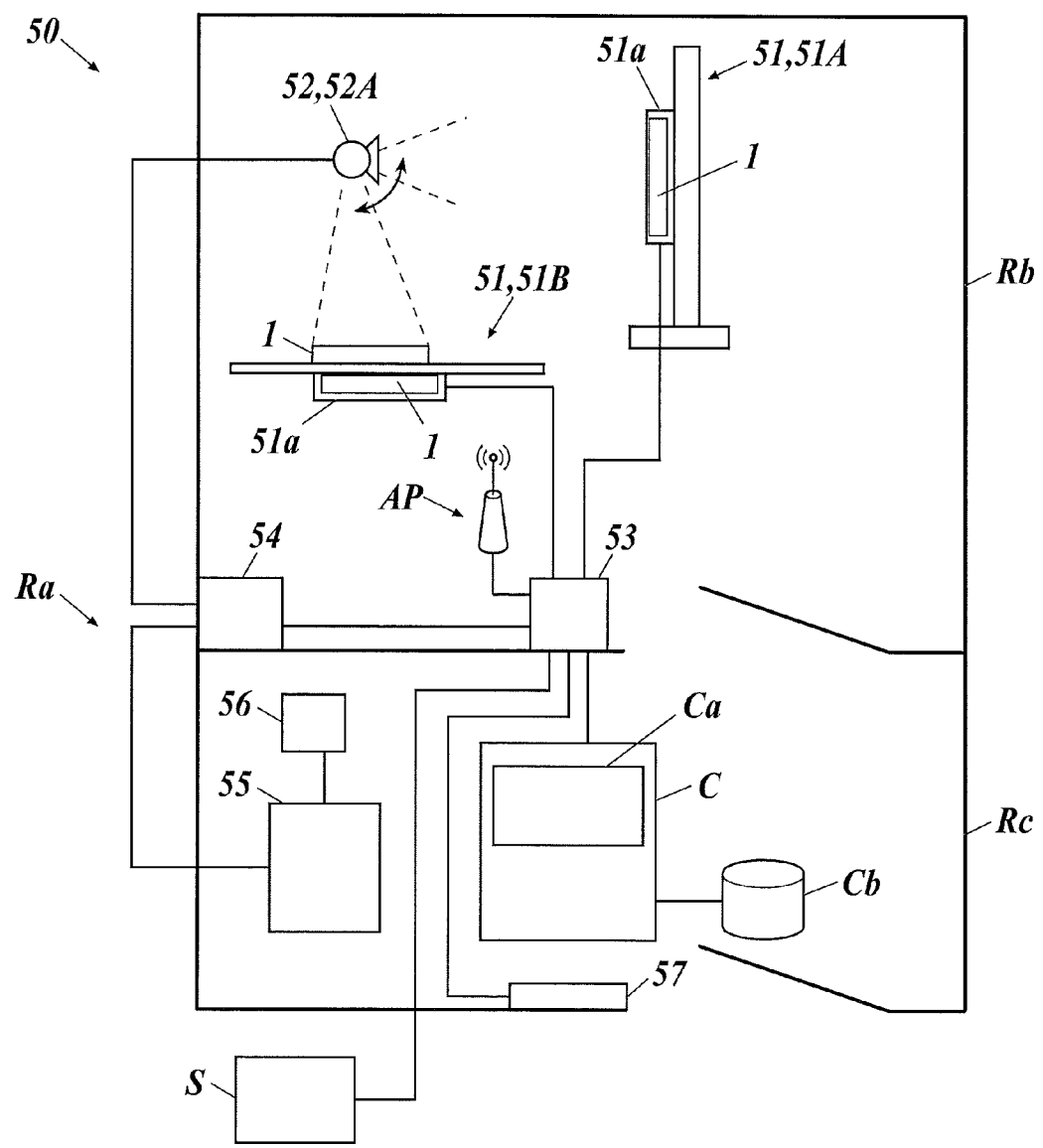
FIG. 8 is a view illustrating a configuration example of the radiographic image photographing system including one photographing room and one console.

For example, as can be seen from FIG. 8, the present invention can also be applied to the case that the radiographic image photographing system 50 includes one photographing room Ra and one console C.

In such case, as illustrated in FIG. 8, the management apparatus S can be provided as a computer separated from the console C. Although not illustrated, it is also possible not to provide the management apparatus S. The console C can be constituted so as to have the function of the management apparatus S.

For example, as illustrated in FIG. 9, the present invention is also applied to the radiographic image photographing system 50 in which the consoles C are connected to the respective photographing rooms Ra, each of which includes the access point AP, the repeater 53, and the tag reader 57 as the information acquisition member, through the network N.

In this case, since the console C is not correlated in one-on-one with the photographing room Ra unlike the embodiment in FIG. 1, it is necessary to assign the photographing room Ra with the console C. When the operator such as the radiology technician assigns the photographing room Ra using the console C, the management apparatus S manages the console C and the assigned photographing room Ra while correlating them with each other.

By such configuration, when notifying the SSID1 dedicated to the access point AP in the photographing room Ra and notifying the IP address and the like of the console C in the photographing room Ra to the radiographic image photographing device 1 existing in the photographing room Ra, the radiographic image photographing device 1 can properly be notified of the IP address of the console C correlated with the photographing room Ra.

In this case, any of console(s) C may be configured to also exert the function of the management apparatus S.

In the embodiment, the RFID tag is the information presentation member 1a which informs the information on the radiographic image photographing device 1 such as the cassette ID, and the tag reader 57 is the information acquisition member which acquires the information on the radiographic image photographing device 1 in the non-contact manner from the information presentation member 1a of the radiographic image photographing device 1. Alternatively, the information presentation member 1a of the radiographic image photographing device 1 and the information acquisition member which acquires the information on the radiographic image photographing device 1 in the non-contact manner may be constructed in other configurations.

As other configuration, for example, the wireless communication may be conducted based on a short-distance wireless communication standard such as ZIGBEE (registered trademark) and Bluetooth (registered trademark), or infrared communication may be conducted.

Moreover, for example, a configuration where a barcode is provided onto the casing 2 (see FIG. 2) of the radiographic image photographing device 1 as the information presentation member 1a (see FIG. 1) so as to code and display the information on the radiographic image photographing device 1 such as the cassette ID, and a barcode reader 51c (see FIG. 5) is provided in a cassette retention section 51a of the bucky device 51 as the information acquisition member can be adopted. In this case, the barcode reader 51c is disposed in the position where the barcode reader 51c can automatically read the barcode of the radiographic image photographing device 1 to readout the information on the radiographic image photographing device 1 when the radiographic image photographing device 1 is loaded into the cassette retention section 51a.

Figure 10A:
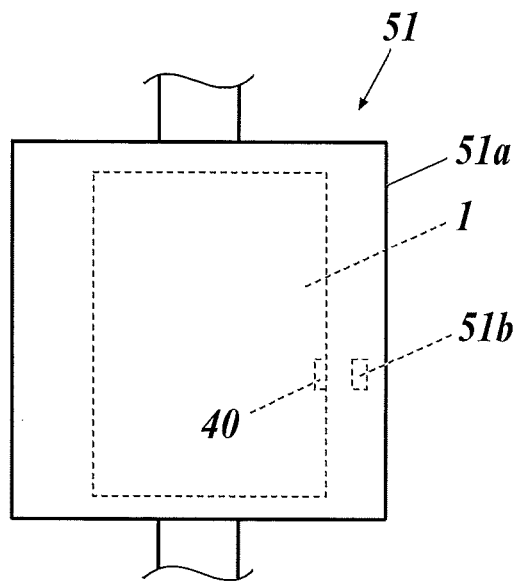
FIG. 10A is a view illustrating a positional relationship between a light receiving member provided in a cassette retention section of a bucky device and an indicator of the radiographic image photographing device, and illustrating the case that the radiographic image photographing device is vertically loaded.
Figure 10B:
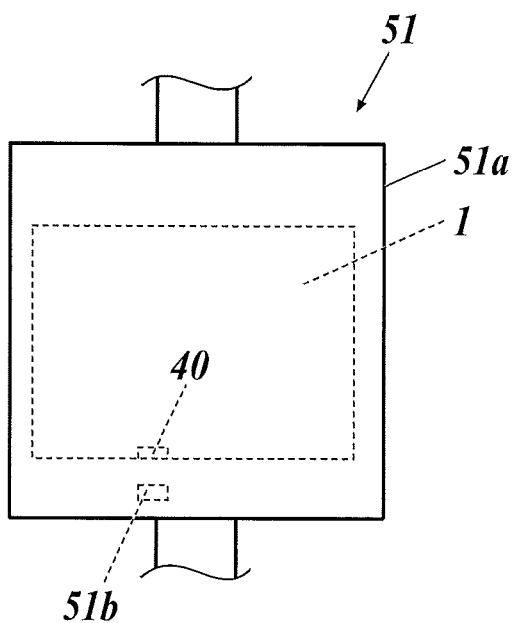
FIG. 10B is a view illustrating the positional relationship between the light receiving member provided in the cassette retention section of the bucky device and the indicator of the radiographic image photographing device, and illustrating the case that the radiographic image photographing device is horizontally loaded.

Furthermore, for example, the indicator 40 of the radiographic image photographing device 1 may be used as the information presentation member. In this case, as illustrated in FIGS. 5, 10A and 10B for example, a light receiving member 51b is disposed as the information acquisition member in the cassette retention section 51a of the bucky device 51 so as to receive the light of the indicator 40 as the information presentation member of the radiographic image photographing device 1.

The indicator 40 as the information presentation member is configured to repeat the operation in which the indicator 40 is turned on for one (1) second and turned off for two seconds, for example. Depending on the way of blinking of the indicator while being turned on for one (1) second, the light receiving member 51b as the information acquisition member is notified of the information on the radiographic image photographing device 1 such as the cassette ID.

Figure 11A:
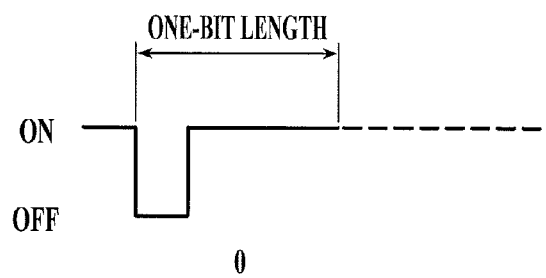
FIG. 11A is a view illustrating an example of a blinking pattern in which a pulse code modulation technology is used, and illustrating the blinking pattern expressing zero (0)
Figure 11B:
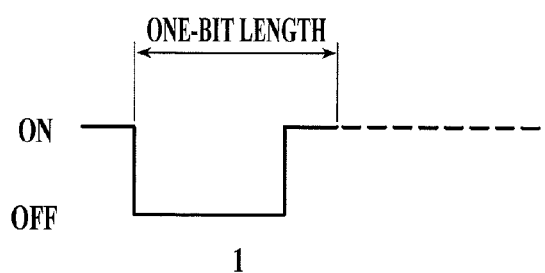
FIG. 11B is a view illustrating an example of the blinking pattern in which the pulse code modulation technology is used, and illustrating the blinking pattern expressing one (1)

Specifically, for example, using a technology of pulse code modulation (PCM), in the case that one (1) millisecond is set to one (1) bit length, a blinking pattern in which a turn-off period is shorter during 1 bit length is set to zero (0) and a blinking pattern in which a turn-off period is longer during 1 bit length is set to one (1) as illustrated in FIG. 11A.

Figure 12:
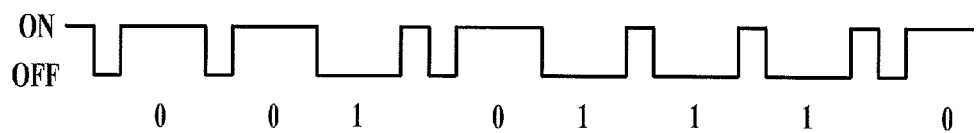
FIG. 12 is a view illustrating an example of information formed by a combination of one (1) and zero (0) signal patterns.

For example, as illustrated in FIG. 12, the indicator 40 is configured to transmit information in which the blinking patterns of one (1) and zero (0) are combined, and by making the indicator 40 blink according to the combination of blinking patterns of one (1) and zero (0) while the indicator is turned on for one (1) second, the indicator 40 as the information presentation member notifies the light receiving member 51b as the information acquisition member of the information on the radiographic image photographing device 1 such as the cassette ID.

For example, the light receiving member 51b as the information acquisition member is connected to the console C through a cable (not illustrated) or the repeater 53, decodes the information on the radiographic image photographing device 1 including the cassette ID from the detected blinking patterns of the indicator 40 of the radiographic image photographing device 1, and transmits the decoded information on the radiographic image photographing device 1 to the console C. Alternatively, the light receiving member 51b may directly transmit the detected blinking patterns to the console C, and the console C may decode the information on the radiographic image photographing device 1 including the cassette ID.

At this point, the indicator 40 of the radiographic image photographing device 1 repeats the one (1)-second lightning described above. Therefore, when contents of the pieces of information on the radiographic image photographing device 1, which are decoded in each one (1)-second lightning of the indicator 40, successively agree with each other, the light receiving member 51b as the information acquisition member or the console C which receives the blinking pattern transmitted from the light receiving member 51b may perform the processing while determining that the information is correct.

Sometimes the radiographic image photographing device 1 is vertically loaded into the cassette retention section 51a as illustrated in FIG. 10A, and sometimes the radiographic image photographing device 1 is horizontally loaded into the cassette retention section 51a as illustrated in FIG. 10B.

Therefore, in order to be able to accurately receive the light emitted from the indicator 40 of the radiographic image photographing device 1 in each case, preferably the light receiving members 51b as the information acquisition members are disposed in at least two positions in FIGS. 10A and 10B in the cassette retention section 51a.

By disposing the light receiving members 51b as the information acquisition members in the positions where the light emitted from the indicators 40 as the information presentation members 1a can be received in both of the cases that the radiographic image photographing device 1 is vertically loaded and that the radiographic image photographing device 1 is horizontally loaded, whether the radiographic image photographing device 1 is loaded vertically or horizontally can be advantageously understood based on which light receiving member 51b receives the light of the indicator 40 without taking out the radiographic image photographing device 1 loaded into the cassette retention section 51a.

The indicator 40 of the radiographic image photographing device 1 originally has a function to notify the operator of the operating state of the radiographic image photographing device 1 and/or a remaining amount of the battery 24 by a lighting color. When the indicator 40 is configured such that the blinking is repeated during one (1)-second lighting as described above, the blinking is repeated at short intervals of, for example, one (1) millisecond.

Even when the blinking is repeated during one (1)-second lighting, actually human eyes feel slightly dark in the light of the indicator 40, and feel the state in which a predetermined color is lit for one (1) second and turned off for two second. Therefore, even when the notification of the information is made by the blinking at extremely short intervals during one (1) second, actually an adverse effect is not generated on the original purpose the operator is notified of the information by the lighting color.

Meanwhile, by applying the technology of notifying the information on the radiographic image photographing device 1 using the blinking pattern, the state of the radiographic image photographing device 1 can be understood without taking out the radiographic image photographing device 1 loaded into the cassette retention section 51*a* of the bucky device 51.

Concretely, as the information on the radiographic image photographing device 1 which is informed to the light receiving member 51*b* as the information acquisition member from the indicator 40 as the information presentation member of the radiographic image photographing device 1, in addition to the cassette ID of the radiographic image photographing device 1 described above, the network setting information (for example, the IP address on the network) and the information on the operating state of the radiographic image photographing device 1 such as a busy state of the radiographic image photographing device 1 and generation of an error (for example, the radiation image photographing cannot be performed or the image data D cannot be transmitted) can be informed.

Also other information such as a cassette type (or a cassette size such as 14×17 inch and 17×17 inch) of the radiographic image photographing device 1, a type of the scintillator 3 (see FIG. 3), the remaining amount of the battery 24 (see FIG. 4), and receiving radio wave intensity (a so-called radio wave state) detected by the wireless communication section 42 can be informed by the blinking pattern of the indicator 40 of the radiographic image photographing device 1.

The console C is configured to display the decoded information on the radiographic image photographing device 1 on a display section Ca as needed basis such that the operator such as the radiology technician issues the instruction, when the information on the radiographic image photographing device 1 is transmitted from the light receiving member 51*b* as the information acquisition member.

As shown in FIG. 5, a configuration where the display member D composed of a CRT or an LCD is provided in the photographing room Ra, for example, near the bucky device 51, and the console C makes the display member D display the same information as the content displayed on the display section Ca of the console C, namely, the information on the cassette ID or operating state of the radiographic image photographing device, can be adopted.

Moreover, as shown in FIG. 5, also a configuration where the operator such as the radiology technician brings with the mobile terminal T including the display screen Ta, and the console C transmits to the mobile terminal T the same information as the content displayed on the display section Ca of the console C, namely, the information on the cassette ID or operating state of the radiographic image photographing device so that the mobile terminal T displays the information on the display screen Ta, can be adopted.

It is also possible to provide a rotary beacon light as the display member in the photographing room Ra, which light gives a warning by lighting in the case that the console C determines that abnormal information, for example information that the battery 24 almost runs out, exists in the decoded information on the radiographic image photographing device 1.

According to the above-described configuration, advantageously the operator such as the radiology technician can check the cassette ID or operating state of the radiographic image photographing device 1 by seeing the display on the display section Ca of the console C or the display member without taking out the radiographic image photographing device 1 loaded into the cassette retention section 51*a* of the bucky device 51.

In addition, for example, when seeing the display on the display section Ca of the console C or the display member, the operator such as the radiology technician can recognize which radiographic image photographing device 1 is loaded into the bucky device 51 without taking out the radiographic image photographing device 1 loaded into the bucky device 51.

Thus, when the radiographic image photographing device 1 loaded into the bucky device 51 is the radiographic image photographing device 1 which should originally be used, the radiation image photographing can be performed without an additional operation. When the radiographic image photographing device 1 loaded into the bucky device 51 is not the radiographic image photographing device 1 which should originally be used, the proper radiographic image photographing device 1 can be loaded again to perform the radiation image photographing.

Therefore, it becomes possible to accurately prevent the generation of the problem in that the radiation image photographing is performed again to increase the dose of the radiation and a burden on the patient because the radiation image photographing is performed using the radiographic image photographing device 1 which should not be used.

Furthermore, it is also possible to easily and accurately recognize the operating state of the radiographic image photographing device 1, namely, the busy state, the generation of the error, the remaining amount of the battery 24, and the radio wave state only by seeing the display on the display section Ca of the console C or the display member without taking out the radiographic image photographing device 1 loaded into the bucky device 51.

Therefore, the operator such as the radiology technician can accurately recognize these pieces of information to take proper action as needed basis.

According to the above configuration, the operator such as the radiology technician can accurately recognize the state of the radiographic image photographing device 1 only by seeing the display on the display section Ca of the console C or the display member without taking out the radiographic image photographing device 1 loaded into the bucky device 51. Because the operator can take proper action as needed basis, the radiographic image photographing system 50 has great usability for the operator.

Incidentally, when the light receiving members 51*b* as the information acquisition members are disposed at least two positions in the cassette retention section 51*a* of the bucky device 51 as illustrated in FIGS. 10A and 10B, advantageously the vertical or horizontal loading of the radiographic image photographing device 1 into the cassette retention section 51*a* can easily and accurately be understood based on which light receiving member 51*b* receives the light of the indicator 40, without taking out the radiographic image photographing device 1 loaded into the bucky device 51, as described above.

The present invention is not limited to the embodiments, and various changes can be made without departing from the scope of the present invention.

What is claimed is:

1. A radiographic image photographing system comprising:
   a plurality of photographing rooms;
   a portable radiographic image photographing device which comprises: a plurality of radiation detection elements arrayed in a two-dimensional pattern; a wireless communication member structured to conduct wireless communication with an access point; and an information presentation member structured to present identification information on the radiographic image photographing device;

a console which is communicable with the radiographic image photographing device;

the access point, which is structured to conduct wireless communication with the wireless communication member in the radiographic image photographing device and relay communication conducted between the wireless communication member in the radiographic image photographing device and the console;

an information acquisition member structured to acquire the identification information on the radiographic image photographing device from the information presentation member in the radiographic image photographing device in a non-contact manner; and a management apparatus to which at least the access point and the information acquisition member are connected, wherein the information acquisition member is structured to notify the management apparatus of the identification information on the radiographic image photographing device, which is acquired from the information presentation member in the radiographic image photographing device, the management apparatus is structured to notify the wireless communication member in the radiographic image photographing device of an identifier dedicated to the access point correlated with the information acquisition member when the identification information on the radiographic image photographing device is received, the wireless communication member in the radiographic image photographing device comprises a general-purpose identifier which enables communication with the access point, the wireless communication member receives the dedicated identifier from the management apparatus by conducting wireless communication with the access point using the general purpose identifier, and the wireless communication member conducts communication with the access point using the identifier dedicated to the access point after the management apparatus notifies the wireless communication member in the radiographic image photographing device of the identifier dedicated to the access point;

wherein the access point, the information acquisition member, and a repeater to which the access point and the information acquisition member are connected, are provided in each of the plurality of photographing rooms, the management apparatus is connected to the repeater in each of the photographing rooms through a network, the general-purpose identifier is an identifier common to the access point in each of the photographing rooms, and the identifier dedicated to the access point is an identifier which is assigned to the access point in each of the photographing rooms and different from the identifier assigned to the access point in other of the photographing rooms.

2. The radiographic image photographing system of claim 1, wherein at least one of the information acquisition member and the repeater is structured to notify the management apparatus of the identification information on the radiographic image photographing device while attaching identification information of the information acquisition member and/or the repeater to the information on the radiographic image photographing device, at least one of the pieces of the identification information of the information acquisition member and the repeater is previously correlated with the photographing room, and when the information acquisition member is structured to notify the management apparatus of the identification information on the radiographic image photographing device, which is acquired from the information presentation member in the radiographic image photographing device, the management apparatus is structured to perform management by recognizing which of the photographing rooms the radiographic image photographing device exists in based on the identification information on the radiographic image photographing device.

3. The radiographic image photographing system of claim 1, wherein the console is provided in each of the photographing rooms.

4. The radiographic image photographing system of claim 1, wherein the console is connected to each of the photographing rooms through the network, and the management apparatus is structured such that when one of the photographing rooms is assigned by the console, the management apparatus manages the console and the photographing room assigned by the console while correlating the console and the assigned photographing room with each other.

5. The radiographic image photographing system of claim 1, wherein the management apparatus is structured to notify the wireless communication member in the radiographic image photographing device of both the identifier dedicated to the access point correlated with the information acquisition member and an address of the console on a network.

6. The radiographic image photographing system of claim 1, wherein the identification information on the radiographic image photographing device comprises the identification information of the radiographic image photographing device.

7. The radiographic image photographing system of claim 1, wherein the information presentation member in the radiographic image photographing device is a barcode which displays the identification information on the radiographic image photographing device, and the information acquisition member is a barcode reader structured to read the identification information on the radiographic image photographing device from the barcode.

8. The radiographic image photographing system of claim 1, wherein the information presentation member in the radiographic image photographing device is an RFID tag, and the information acquisition member is a tag reader structured to acquire the identification information on the radiographic image photographing device from an electromagnetic field or a radio wave emitted from the RFID tag in a non-contact manner.

9. The radiographic image photographing system of claim 1, wherein the information presentation member in the radiographic image photographing device is a light emission member structured to make a notification of the identification information on the radiographic image photographing device by blinking of light, and the information acquisition member is a light receiving member structured to receive the light emitted from the light emission member and acquires the identification information on the radiographic image photographing device from a blinking pattern of the light in the non-contact manner.

10. The radiographic image photographing system of claim 9, further comprising a bucky device including a cassette retention section into which the radiographic image photographing device can be loaded,
wherein the information acquisition member is provided in the cassette retention section of the bucky device.

11. The radiographic image photographing system of claim 10, wherein the information acquisition member is disposed in each of positions where the light emitted from the information presentation member in the radiographic image photographing device can be received when the radiographic image photographing device is vertically loaded into the cassette retention section of the bucky device and where the light emitted from the information presentation member can be received when the radiographic image photographing device is horizontally loaded into the cassette retention section.

12. The radiographic image photographing system of claim 1, wherein the identification information on the radiographic image photographing device comprises an operating state of the radiographic image photographing device and a network setting.

13. The radiographic image photographing system of claim 1, further comprising a photographing room,
wherein the photographing room comprises a display member which displays the identification information on the radiographic image photographing device, which is transmitted from the console.

14. The radiographic image photographing system of claim 1, wherein the console is structured to transmit the identification information on the radiographic image photographing device to a mobile terminal brought with an operator, and make the mobile terminal display the identification information on the radiographic image photographing device on a display screen in the mobile terminal.

15. The radiographic image photographing system of claim 13, wherein the display member comprises a CRT or an LCD.

16. The radiographic image photographing system of claim 13, wherein the display member comprises a rotary beacon light.

* * * * *